United States Patent [19]
Cooley et al.

[11] Patent Number: 5,817,745
[45] Date of Patent: Oct. 6, 1998

[54] CATALYST COMPOSITIONS

[75] Inventors: Neil Andrew Cooley, Teddington; Evert Jan Ditzel, Goole, both of England

[73] Assignee: BP Chemicals Limited, London, England

[21] Appl. No.: 684,017

[22] Filed: Jul. 19, 1996

[30] Foreign Application Priority Data

Jul. 21, 1995 [GB] United Kingdom ............ 9515098

[51] Int. Cl.⁶ .................................. C08G 67/02
[52] U.S. Cl. .................... 528/392; 528/398; 528/399
[58] Field of Search .................. 528/271, 392, 528/398, 399; 502/185; 556/13, 16; 568/8

[56] References Cited

U.S. PATENT DOCUMENTS

| | | |
|---|---|---|
| 3,694,412 | 9/1972 | Nozaki . |
| 5,175,244 | 12/1992 | Budzelaar et al. ............ 528/392 |
| 5,359,028 | 10/1994 | Drent et al. ............ 528/392 |
| 5,468,708 | 11/1995 | Cooley et al. ............ 502/162 |

FOREIGN PATENT DOCUMENTS

| | | |
|---|---|---|
| 121965 | 10/1984 | European Pat. Off. . |
| 181014 | 5/1986 | European Pat. Off. . |
| 222454 | 5/1987 | European Pat. Off. . |
| 88201803.9 | 8/1988 | European Pat. Off. . |
| 619335 | 10/1994 | European Pat. Off. . |

OTHER PUBLICATIONS

"Bifunktionelle Aminophosphane $(Et_2N_2P—[CH_2]_n—P(NEt_2)_2$ und $Et_2N(R)P—[CH_2]_n—P(R)NEt_2$"; *Zur Kenntnis der Organophosphorverbindungen XX*; K. Diemert et al.; vol. 15, pp. 155–164; ©1983.

"Synthese und Eigenschaften bifunktioneller Organobromphosphane"; *Zur Kenntnis der Organophosphorverbindungen XIX*; Chem. Ber. 115, pp. 1947–1955; ©1982.

*Primary Examiner*—Duc Truong
*Attorney, Agent, or Firm*—Fay, Sharpe, Beall, Fagan, Minnich & McKee

[57] ABSTRACT

A process for the manufacture of polyketones wherein carbon monoxide and at least one olefin are polymerized in the presence of a catalyst. The catalyst is prepared by reacting together a promotor; a source of a Group VIII metal; and a compound of the formula $A_2PR^1PA_2$ wherein each A is independently a hydrocarbyl group or a Group B bonded to the phosphorous of the $PA_2$ moiety directly through a nitrogen, sulphur or oxygen and $R^1$ is a divalent organic group, with the proviso that at least one of the two A groups bonded to each phosphorous is a Group B.

8 Claims, No Drawings

CATALYST COMPOSITIONS

The present invention relates to catalyst compositions and to processes for preparing interpolymers of olefins and carbon monoxide by polyrerising a mixture of one or more olefins and carbon monoxide in the presence of such catalyst compositions. In particular, the present invention relates to novel compounds and their use in catalysts for such processes.

The preparation of linear alternating interpolymers of olefins and carbon monoxide having the formula:

$$[(CR_2-CR_2)_n\overset{O}{\underset{\|}{C}}]_m$$

where the R groups are independently hydrogen or hydrocarbyl groups, n is at least 1 and m is a large integer, known from U.S. Pat. No. 3,694,412. Such linear alternating interpolymers, which hereafter will be called polyketones, are prepared according to U.S. Pat. No. 3,694,412 by polymerising a mixture of one or more olefins and carbon monoxide in the presence of an aryl phosphine complex of a palladium halide and an inert solvent, However, the processes described in U.S. Pat. No. 3,694,412 are s low even at elevated temperature and pressure.

An improved version of the process described in U.S. Pat. No. 3,694,412 is described in European patent applications 181014 and 121965. It was subsequently found that the rate of the polymerisation process could be increased considerably by using a palladium catalyst with inter alia a bidentate phosphine and the anion of a carboxylic acid having a pKa of lower than 2 (as measured in aqueous solution). Examples of anions which can be used include trichloroacetate, dichloroacetate, tetrafluoroborate, hexafluorophosphate and p-toluene sulphonate, such anions being respectively the conjugate anions of trichloroacetic acid, dichloroacetic acid, tetrafluoroboric acid, hexafluorophosphoric acid and p-toluenesulphonic acid.

More recently EP 222454 suggests that any acid having a pKa of less than 5 (determined in aqueous solution at 18° C.) can be used.

It has now been found that instead of using a bidentate diphosphine as described in EP 121965, catalyst systems, in particular palladium catalyst systems, for the production of polyketones based upon novel phosphine ligands can be employed.

According to the present invention there is provided a catalyst composition prepared by reacting together:
(a) a source of a Group VIII metal,
(b) a compound of the formula (I)

$$A_2PR^1PA_2 \qquad\qquad I$$

where each A is independently a hydrocarbyl group or a group B such that B is bonded to the phosphorus of the $PA_2$ moiety directly through a nitrogen, sulphur or oxygen and $R^1$ is an divalent organic group with the proviso that at least one of the two A groups bonded to each phosphorus is a group B, and
(c) a promoter.

The present invention further provides a process for preparing polyketones by polymerising a mixture of carbon monoxide and one or more olefins in the presence of a catalyst composition as defined hereinabove.

The term polyketone is used herein to mean an interpolymer of one or more olefins with carbon monoxide. The idealised structure of such a material would comprise a one, two or three dimensional network of strictly alternating olefin and carbon monoxide units. Although polyketones prepared according to the present invention correspond to this idealised structure, it is envisaged that materials corresponding to this structure in the main but containing small regimes (i.e. up to 10 wt %) of the corresponding polyolefin also fall within the definition.

The catalyst composition described above is itself prepared by reacting together (a) a source of a Group VIII metal, (b) a compound having the formula (I) defined above, and (c) a promoter.

As regards component (a), this is a source of a Group VIII metal, the Group VIII metals are iron, cobalt, nickel, ruthenium, rhodium, palladium, osmium, iridium and platinum. The second-row Group VIII metals (i.e. ruthenium, rhodium, palladium) are preferred; particularly preferred is palladium.

Component (b) is a compound of formula I $$A_2PR^1PA_2 \qquad\qquad I.$$

where each A is independently a hydrocarbyl group or a group B such that B is bonded to the phosphorus of the $PA_2$ moiety directly through a nitrogen, sulphur or oxygen and $R^1$ is an divalent organic group with the proviso that at least one of the two A groups bonded to each phosphorus is a group B.

Where A is a hydrocarbyl group it can be for example a substituted or unsubstituted alkyl, cycloalkyl or aryl group preferably an aryl group e.g. phenyl or methoxy phenyl; $R^1$ is a divalent organic group, for example, $-(CR^2R^3)n-$ where $R^2$ and $R^3$ are independently a hydrogen or a $C_1$–$C_6$ alkyl group and each of the $CR^2R^3$ groups can be the same or different and n is an integer from 1 to 6; however, it is preferred that $R^2$ and $R^3$ are each hydrogen and n is an integer from 1 to 6, preferably 1 to 4, more preferably n is 3. Rcan also be an aromatic group e.g. phenyl or naphthyl, preferably connected to the phosphorus atoms through adjacent atoms.

At least one of the two A groups bonded to each phosphorus atom is the group B. The group B is a group that is bonded to the phosphorus of the $PA_2$ moiety directly through a nitrogen, sulphur or oxygen. The group B can for example be $-OR$, $-SR$ or $-NR2$ where R is hydrogen or a hydrocarbyl group, for example a substituted or unsubstituted alkyl, cycloalkyl or aryl group preferably an alkyl group for example a $C_1$–$C_6$ alkyl preferably methyl or ethyl. Where B is $-NR2$, R is preferably a $C_1$–$C_6$ alkyl, for example methyl or ethyl, alternatively the two R groups together with the nitrogen atom can form a heterocyclic ring, for example a pyrrole ring.

As regards component (c) which is a promoter, this can be a source of an anion which is either non-coordinating or weakly coordinating. Such anions are suitably the conjugate bases of strong acids having e.g. a pKa of less than 6 preferably less than 2 (e.g. $HBF_4$, $HPF_6$, $HSbF_6$, paratoluene sulphonic acid). Alternatively, the promoter can be a boron hydrocarbyl compound for example a boron alkyl or boron aryl compound. In particular the Boron hydrocarbyl compound can be a Lewis acid of the formula BXYZ where at least one of X Y and Z is a monovalent hydrocarbyl group.

Where any one of X Y or Z is a monovalent hydrocarbyl group, it is suitably an alkyl for example a $C_1$–$C_6$ alkyl group, or an aryl group for example, a substituted or unsubstituted phenyl group for example $C_6H_5$ or $C_6F_5$. Other suitable monovalent hydrocarbyl groups are p-Hal $C_6H_4$ (where Hal=F,Cl,Br), m, m-$C_6H_3(CF_3)_2$, $CF_3$ and $C_2F_5$. It is to be understood that two or three of the groups X, Y and Z can together form bi or trivalent groups respectively. At least one of X, Y and Z is a monovalent hydrocarbyl group; however it is preferred that at least two, preferably three, of X, Y and Z are each monovalent hydrocarbyl groups. Suitable examples of such Lewis acids are $BMe_3$, $BEt_3$, $B(C_6H_5)_3$, $B[mm\text{-}(CF_3)_2C_6H_3]_3$, $B(mesityl)_3$, $B(p\text{-}Hal\ C_6H_4)_3$ (where Hal =F, Cl, Br), $B(m\text{-}CF_3C_6H_4)_3$ and $B(C_6F_5)_3$, preferably $B(p\text{-}Hal\ C_6H_4)_3$ and $B(C_6F_5)_3$. Where one or more of X, Y and Z is not a hydrocarbyl group, it is suitably a OH, OR or halide group preferably a halide group for example fluoride, chloride or bromide especially fluoride. Examples of compounds where one of X, Y, Z is a group other than a hydrocarbyl group are boronic acids of the formula $RB(OH)_2$ where R is a hydrocarbyl group e.g. $PhB(OH)_2$, and hydrocarbyl 1, 3, 2-benzodioxaboroles.

Other suitable boron hydrocarbyl compounds for use in this invention are borate salts of the formula MBR4 where M is an alkali metal e.g. Li, Na, and R is a hydrocarbyl group e.g. $C_6H_5$, $C_6F_5$ and substituted analogues. For example a suitable compound could be $LiB(C_6F_5)_4$ or $NaB(C_6H_5)_4$.

When a boron hydrocarbyl compound is used, for example a Lewis Acid BXYZ it is added to the reaction medium in an amount such that the Group VIII metal: Boron ratio is in the range 10:1 to 1:200 preferably 1:1 to 1:100 more preferably 1:5 to 1:70 e.g. 1:50.

Where the Group VIII metal is palladium, the source of palladium can include simple inorganic and organic salts, e.g. halides, nitrates, carboxylates and the like as well as organometallic and coordination complexes. In some cases, by suitable choice of coordination complex, it may be possible to add the palladium and the compound of formula I as a single entity.

For example the novel compounds of formula II

$L_2Pd(P\text{—}P)$ (II)

where each L is independently a monodentate ligand or $L_2$ taken together is a bidentate ligand and P—P is a compound of the formula I, $A_2PR^1PA_2$, where A and $R^1$ have the meanings assigned to them as hereinabove, can be used together with component (c), a promoter. L in formula II is typically a halide or carboxylate ligand for example $CH_3COO$ or $CF_3COO$. In a further aspect of the present invention there are provided compounds of formula II as defined above.

Where the promoter is a source of a non-coordinating or weakly coordinating anion, this can also be incorporated into a discrete compound as a counter anion.

For example, novel compounds of the formula III can be used.

$[L_2Pd(P\text{—}P)](A^1)_2$ (III)

where L and P—P have the same meanings assigned to them as in formula II above and $A^1$ is a non-coordinating or weakly coordinating anion. L is preferably a 2-electron donor ligand eg. $H_2O$, ROH (where R is a hydrocarbyl group eg. Me, Ph), $R_2$ CO (where each R is independently a hydrocarbyl group eg. Me). L is typically benzonitrile. An example of a compound of formula III is [(benzonitrile)$_2$Pd (P—P)] (BF$_4$)$_2$ where P—P is PhP(NEt$_2$) (CH$_2$)$_3$ P(NEt$_2$) Ph.

In a further aspect of the present invention, there are provided compounds of the formula III.

Alternatively, the anion can be used in the form of a salt or its conjugate acid together with the Group VIII metal and the compound of formula I whether the latter two are added as a single discrete compound or are added as two components.

Although any source of the Group VIII metal can be used, it may be necessary, when a metal complex having strongly coordinating ligands is employed, to ensure that such ligands are removed. An example of such a complex is palladium acetate where the acetate groups bind to the palladium. In such cases the acetate groups can be removed by adding component (c) above for example, as the conjugate acid of a non-coordinating or weakly coordinating anion since such a conjugate acid will protonate the acetate groups and cause their removal.

Another approach which is useful when metal halides e.g. palladium halides are employed (halide anions also bind strongly to the palladium) is to use a thallium or silver salt of a non-coordinating or weakly coordinating anion. In such cases a metathesis reaction occurs and the insoluble silver or thallium halide precipitates and can be removed by filtration.

Considering next the feedstocks for the polymerisation reaction, it is believed that any source of carbon monoxide can be used. Thus the carbon monoxide may contain nitrogen, inert gases and up to 10% hydrogen.

Any olefin can in theory be used although the best reaction rates are obtained when either ethylene or a mixture of ethylene and at least one other olefin e.g. ethylene/propylene and the like, is used. The lower rates obtained in the absence of ethylene should not be construed as indicating that the process can be used only with an ethylene feedstock since other olefins such as propylene, 4,methylpentene-1, styrene, acrylates, vinyl acetates and the like all undergo reaction to some extent. A preferred polyketone is a terpolymer of ethylene, propylene and carbon monoxide; under these circumstances the olefin will be a mixture of ethylene and propylene.

The catalyst compositions can be used in either the gas-phase or the liquid-phase. It is to be understood that the term liquid phase also includes slurry-phase where the polyketone product is insoluble in the reaction solvent.

Where the polymerisation process is in the liquid phase it is suitably carried out in a solvent which is chemically inert under the conditions employed and one in which the catalyst is soluble. Examples of such solvents include alcohols, e.g. methanol, ethanol and propanol, ethers, glycols, glycol ethers and chlorinated solvents e.g. chloroform and dichloromethane. Preferred solvents are methanol, ethoxyethanol, chloroform or dichloromethane especially dichloromethane. Alternatively, an aliphatic tertiary alcohol can be used, preferably tertiary butanol. This can be used as a solvent on its own or in combination with an aprotic solvent, e.g. ketones. A preferred solvent system is tertiary butanol/acetone mixture.

The polymerisation process is suitably carried out at a temperature in the range 20° to 150° C. preferably 50° to 120° C. and at elevated pressure (e.g. I to 100 bars). The overpressure of gas is suitably carbon monoxide or carbon monoxide and olefin, if the olefin is gaseous under the reaction conditions. It is possible to operate the polymerisation process either batchwise or continuously.

The invention will be illustrated with reference to the following Examples:

EXAMPLE 1

PhP(NEt$_2$)(CH$_2$)$_3$P(NEt$_2$)Ph was prepared as follows:

A solution of PCl$_3$ (15cm$^3$, 0.171 mol) in diethyl ether (50cm$^3$) was added over a ten minute period to a suspension of PhP(Li)(CH$_2$)$_3$P(Li)Ph (6.756 g, 24.8 mmol), prepared by a published procedure (Powell J, Lough A, Wang F; Organometallics 1992, 11, 2289), in diethyl ether (100 cm$^3$) at −78° C. The reaction mixture was stirred for 30 minutes and then allowed to warm to ambient temperature. After stirring for a further 30 minutes the reaction mixture was filtered and the volatile components were evaporated from the filtrate giving PhP(Cl)(CH$_2$)$_3$P(Cl)Ph as a pale yellow oil. The PhP(Cl)(CH$_2$)$_3$P(Cl)Ph was redissolved in diethyl ether (50cm$^3$) and cooled to −78° C. Diethylamine (15 cm$^3$, 0.145 mol) was added, the reaction mixture was filtered and the volatile components were evaporated. The resulting oil was purified by short path vacuum distillation with a Kugelrohr apparatus to give Php(NEt$_2$)(CH$_2$)$_3$P(NEt$_2$)Ph (1.4763 g, 3.67 mmol) as a colourless oil. $^{31}$p{$^1$H}NMR (CD$_2$Cl$_2$)= 56.3, 56.6 ppm.

EXAMPLE 2

PhP(NC$_4$H$_4$)(CH$_2$)$_3$P(NC$_4$H$_4$)Ph was prepared by a similar procedure to that detailed in Example 1 with the following differences:

PhP(Li)(CH$_2$)$_3$P(Li)Ph (10.383 g, 38.2 mmol) was employed. Triethylamine (5cm$^3$, 35.9 mmol) and pyrrole (2.15 cm$^3$, 31.0 mmol) were used in place of diethylamine. The product was not purified by distillation. Instead, the crude product was dissolved in toluene (50 cm$^3$) and filtered through silica (2 cm×2cm, 70–260 mm). Removal of the toluene under reduced pressure afforded PhP(NC$_4$H$_4$)(CH$_2$)$_3$P(NC$_4$H$_4$)Ph (2.04g, 5.2 mmol) as needle crystals. $^{31}$P[$^1$H] NMR (CD$_2$Cl$_2$) =45.4 ppm.

EXAMPLE 3

A carbon monoxide/ethene copolymer was prepared as follows.

Dichloromethane (90cm$^3$) was charged to a 300cm$^3$ autoclave under nitrogen. The autoclave contents were then pressurised to 30 bar G with a 1:1 mixture of carbon monoxide and ethene ancl heated to 70° C. A solution of tris(pentafluorophenyl)borane (0.08 g, 0. 16 mmol) in dichloromethane (10 cm$^3$) was introduced, followed by a procatalyst solution comprising PhP(NEt$_2$)(CH$_2$)$_3$P(NEt$_2$)Ph (0.0075 g, 0.019 mmol), prepared as in example 1, and palladium acetate (0.0038g, 0.016mmol) in dichloromethane (10cm$^3$). The pressure was adjusted to 50 bar G by the addition of 1:1 carbon monoxide/ethene, and this pressure was maintained by addition of the aforementioned gas mixture on demand. After 3.0 hours the pressure was released and the reaction was cooled to room temperature. The polymer was collected by filtration and dried under reduced pressure. 10.953 g of copolymer was obtained.

EXAMPLE 4

A carbon monoxide/ethene copolymer was prepared using substantially the same procedure to that detailed in Example 3, with the following differences:

The procatalyst solution comprised PhP(NC$_4$H$_4$)(CH$_2$)$_3$P(NC$_4$H$_4$)Ph (0.0082 g, 0.021mmol), prepared as in Example 3, and palladium acetate (0.0043 g, 0.019 mmol) in dichloromethane (10 cm$^3$). The reaction time was 6.25 hours. 5.648 g of copolymer was forned.

EXAMPLE 5

A carbon monoxide/ethene/propene terpolymer was prepared by substantially the same procedure to that detailed in Example 3 for a carbon monoxide/ethene copolymer, with the following differences:

The autoclave was initially charged with dichloromethane (90 cm$^3$) and propene (25 g, 0.59 mol). The procatalyst solution comprised PhP(NEt$_2$)(CH$_2$)$_3$P(NEt$_2$)Ph (0.0081 g, 0.020 mmol), prepared as in Example 1, and palladium acetate (0.0041 g, 0.018 mmol) in dichloromethane (10cm$^3$). The reaction time was 3.25 hours. 4.00 g of terpolymer was formed. $^{13}$C NMR analysis showed the polymer to be a linear polymer containing alternating units, originating in carbon monoxide, and with units originating in propene comprising 8.1% of the total units.

EXAMPLE 6

A carbon monoxide/ethene/propene terpolymer was prepared by substantially the same procedure to that detailed in Example 5, with the following differences:

The procatalyst solution comprised PhP(NC$_4$H$_4$)(CH$_2$)$_3$P(NC$_4$H$_4$)Ph (0.0077g, 0.020mmol), prepared as in Example 2, and palladium acetate (0.0040g, 0.018mmol) in dichloromethane (10cm$^3$). The reaction time was 3.0 hours. 1.635g of terpolymer was formed. $^{13}$C NMR analysis showed the polymer to be a linear polymer containing alternating units originating in carbon monoxide, and with units originating in propene comprising 7.3% of the total units.

EXAMPLE 7 (COMPARATIVE EXAMPLE)

A carbon monoxide/ethene/propene terpolymer was prepared by substantially the same procedure to that detailed in Example 5, with the following differences:

The procatalyst solution comprised Ph$_2$P(CH$_2$)$_3$PPh$_2$ (0.0074 g, 0.018 mmol), prepared as in Example 2, and palladium acetate (0.0040 g, 0.018 mmol) in dichloromethane (10 cm$^3$). The reaction time was 2.8 hours. 7.960 g of terpolymer was formed. $^{13}$C NMR analysis showed the polymer to be a linear polymer containing alternating units originating in carbon monoxide, and with units originating in propene comprising 6.6% of the total units.

EXAMPLE 8

[Pd{PhP(NEt$_2$)(CH$_2$)$_3$P(NEt$_2$)Ph}(PhCN)$_2$][BF$_4$]$_2$ was prepared as follows:

PhP(NEt$_2$)(CH$_2$)$_3$P(NEt$_2$)Ph (0.9688 g, 2.41 mmol), prepared as in example 1, and (cis,cis-1,5-cyclooctadiene)palladium(II)chloride (0.6721 g, 2.35 mmol) (obtained from Aldrich chemical Co.) were co-dissolved in dichloromethane (10 cm 3) to give an orange solution. Addition of diethyl ether (90 cm$^3$) to the solution gave a orange oil, and decantation of the mother liquor and removal of residual solvent under reduced pressure gave an orange solid. The orange solid was redissolved in dichloromethane (20 cm$^3$) and benzonitrile (5 cm$^3$). Addition of silver tetrafluoroborate (0.9331 g, 4.78 mmol) gave an immediate white precipitate. After stirring for 1h the reaction mixture was filtered and diethyl ether ((100 cm$^3$) was added to the filtrate. The resulting oil was isolated by decantation and redissolved in dichloromethane (20 cm$^3$). The solution was filtered through a celite plug the diethyl ether (100 cm$^3$) was added. Decantion, followed by removal of residual solvent gave yellow microcrystals of
[Pd{PhP(NEt$_2$)(CH$_2$)$_3$P(NEt$_2$)Ph}(PhCN)$_2$][BF$_4$]$_2$ (0.9738g, 1.10 mmol). $^{31}$p{$^1$H} NMR (CD$_2$Cl$_2$): δ(ppm) =61.0, 61.3; $^1$H NMR (CD$_2$Cl$_2$): δ(ppm) =0.9–1.4 (m, CH$_3$, 12H), 2.0–2.8 (m, CH$_2$, 6H), 3.42 and 3.20 (m, NCH$_2$, 8H), 7.0–8.2 (m, Ph, 20H).

EXAMPLE 9

A carbon monoxide/ethene/propene terpolymer was prepared by substantially the same procedure to that detailed in example 5, with the following differences:

The autoclave was initially charged with dichloromethane (90 cm$^3$) and propene (14.6 g, 0.348 mol). Tri(4- chlorophenyl)borane (0.1101 g, 0.319 mmol) was employed in place of tris(pentafluorophenyl)borane. The procatalyst solution comprised $[Pd\{PhP(NEt_2)(CH_2)_3P(NEt_2)Ph\}(PhCN)_2][BF_4]_2$ (0.0450 g, 0.05 mmol), prepared as in example 8, in dichloromethane (10 cm$^3$). The reaction time was 3.00 hours. 29.4 g of terpolymer was formed. $^{13}$C NMR analysis showed the polymer to be a linear polymer containing alternating units originating in carbon monoxide, and with units originating in propene comprising 5.1% of the total units.

We claim:

1. A process for preparing polyketones comprising contacting carbon monoxide and at least one olefin in the presence of a catalyst composition prepared by reacting together:

(a) a source of a Group VIII metal, (b) a compound of the formula (I)

 (I)

where each A is independently a hydrocarbyl group or a group B such that B is bonded to the phosphorus of the PA$_2$ moiety directly through a nitrogen, sulphur or oxygen and R$^1$ is a divalent organic group with the proviso that at least one of the two A groups bonded to each phosphorus is a group B, and (c) a promoter.

2. A process for preparing polyketones as claimed in claim 1 wherein carbon monoxide is polymerised with ethylene and at least one other olefin.

3. The process of claim 1 wherein the Group VIII metal is palladium.

4. The process of claim 1 wherein B is the group NR$_2$ where each R groups is independently a C$_1$ to C$_6$ alkyl group.

5. The process of claim 4 wherein each R group is ethyl.

6. The process of claim 1 wherein the promoter is a source of a weakly-coordinating or non-coordinating anion.

7. The process of claim 1 wherein the promoter is a boron hydrocarbyl compound.

8. The process of claim 7 wherein the boron hydrocarbyl compound is a compound of the formula BXYZ where XY and Z are each independently a monovalent hydrocarbyl group.

* * * * *